United States Patent [19]

Pandey et al.

[11] Patent Number: 6,103,751
[45] Date of Patent: Aug. 15, 2000

[54] CAROTENE ANALOGS OF PORPHYRINS, CHLORINS AND BACTERIOCHLORINS AS THERAPEUTIC AND DIAGNOSTIC AGENTS

[75] Inventors: Ravindra K. Pandey, Williamsville; William R. Potter; Thomas J. Dougherty, both of Grand Island, all of N.Y.

[73] Assignee: Health Research, Inc., Buffalo, N.Y.

[21] Appl. No.: 09/102,417

[22] Filed: Jun. 22, 1998

[51] Int. Cl.[7] .................. A61K 31/40; C07D 487/22
[52] U.S. Cl. .................... 514/410; 540/145; 514/183
[58] Field of Search .................... 540/145; 514/183, 514/410

[56] References Cited

U.S. PATENT DOCUMENTS

| | | | |
|---|---|---|---|
| 4,649,151 | 3/1987 | Dougherty et al. | 514/410 |
| 4,866,168 | 9/1989 | Dougherty et al. | 540/145 |
| 4,889,129 | 12/1989 | Dougherty et al. | 128/664 |
| 4,932,934 | 6/1990 | Dougherty et al. | 604/21 |
| 4,968,715 | 11/1990 | Dougherty et al. | 514/410 |
| 5,002,962 | 3/1991 | Pandey et al. | 514/410 |
| 5,015,463 | 5/1991 | Dougherty et al. | 424/7.1 |
| 5,028,621 | 7/1991 | Dougherty et al. | 514/410 |
| 5,145,863 | 9/1992 | Dougherty et al. | 514/410 |
| 5,198,460 | 3/1993 | Pandey et al. | 514/410 |
| 5,225,433 | 7/1993 | Dougherty et al. | 514/410 |
| 5,238,940 | 8/1993 | Liu et al. | 514/410 |
| 5,286,474 | 2/1994 | Gust, Jr. et al. | 424/7.1 |
| 5,314,905 | 5/1994 | Pandey et al. | 514/410 |
| 5,459,159 | 10/1995 | Pandey et al. | 514/410 |
| 5,498,710 | 3/1996 | Pandey et al. | 540/145 |
| 5,591,847 | 1/1997 | Pandey et al. | 540/472 |
| 5,773,609 | 6/1998 | Robinson et al. | 540/145 |

OTHER PUBLICATIONS

Beems, E. et al., Photosensitizing Properties Of Bacteriochlorophyllin α And Bacteriochlorin α, Two Derivatives Of Bacteriochlorophyll α, Photochemistry and Photobiology, vol. 46, No. 5, pp. 639–643, 1987.

Dougherty T. et al., Photoradiation Therapy. II. Cure Of Animal Tumors With Hematoporphyrin And Light, Journal of the National Cancer Institute, vol. 55, No. 1, pp. 115–119, 1975.

Dougherty, T. et al., Photoradiation Therapy For The Treatment Of Malignant Tumors, Cancer Research, vol. 38, pp. 2628–2635, 1978.

Evensen, J. et al., Photodynamic Therapy Of C3H Mouse Mammary Carcinoma With Haematoporphyrin Di–Ethers As Sensitizers, Br. J. Cancer, 55, pp. 483–486, 1987.

Gomer, C. et al., Determination of [$^3$H]–And [$^{14}$C]Hematoporphyrin Derivative Distribution In Malignant and Normal Tissue, Cancer Research 39, pp. 146–151, 1979.

Henderson, B. et al., An In Vivo Quantitative Structure–Activity Relationship For A Congeneric Series Of Pyropheophorbide Derivatives As Photosensitizers For Photodynamic Therapy[1], Cancer Research 57, pp. 4000–4007, 1997.

Hoober, J. et al., Photodynamic Sensitizers From Chlorophyll: Purpurin–18 And Chlorin $\rho_6$, Photochemistry and Photobiology, vol. 48, No. 5, pp. 579–582, 1988.

(List continued on next page.)

*Primary Examiner*—Mukund J. Shah
*Assistant Examiner*—Pavanaram K Sripada
*Attorney, Agent, or Firm*—Michael L. Dunn

[57] ABSTRACT

A carotene conjugate of the formula:

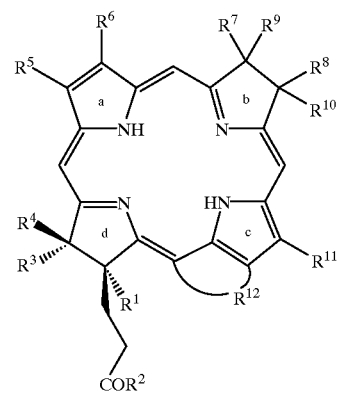

where $R^1$ is hydrogen or methyl; $R^2$ is:

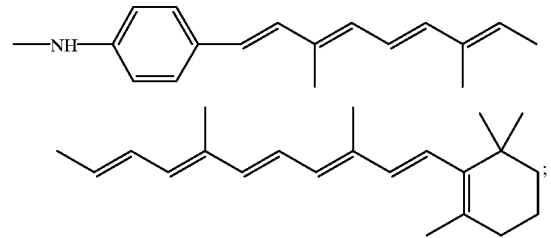

$R^3$, $R^4$ and $R^5$ are independently, hydrogen, methyl or ethyl; $R^6$ and $R^7$ are independently —$R^{13}$, —OR , —$C(R^6)(O)$, —$C(R^{16})_2OR^{13}$, —CH=CHR$^{13}$, or —(CH$_2$)R$^{14}$; $R^8$ is —$R^{13}$, —OR$^{13}$, —$C(R^{16})(O)$, —$C(R^{16})_2OR^{13}$, —CH=CHR$^{13}$, or —(CH$_2$)R$^{14}$ or taken with $R^{10}$ is =O; $R^9$ is —$R^{13}$, —OR$^{13}$, —$C(R^{16})(O)$, —$C(R^{16})_2OR^{13}$, —CH=CHR$^{13}$, or —(CH$_2$)R$^{14}$ or taken with $R^{10}$ is a chemical bond; $R^{10}$ is —$R^{13}$, —OR$^{13}$, —$C(R^{16})(O)$, —$C(R^{16})_2OR^{13}$, —CH=CHR$^{13}$, or —(CH$_2$)R$^{14}$ or taken together with $R^9$ is a chemical bond or taken with $R^8$ is =O; $R^{11}$ is $R^{13}$, or —OR$^{13}$; $R^{12}$ is —$C(R^{13})_2C(Y)$—, —C(O)O(O)C—, —C(NR$^{13}$)O(O)C—, or —C(O)N(R$^{15}$)—C(O)—; $R^{13}$ is, independently at each occurrence, hydrogen or lower alkyl of from 1 through about 10 carbon atoms; $R^{14}$ is an amino acid residue, $R^{15}$ is —$R^{13}$, —$R^{14}$, or —C(O)NHR$^{13}$; $R^{16}$ is, independently at each occurrence, hydrogen or lower alkyl of 1 to about 4 carbon atoms and Y is =O, =S, or 2H—.

38 Claims, 6 Drawing Sheets

OTHER PUBLICATIONS

Lee S. et al., Use Of The Chlorophyll Derivative, Purpurin–18, For Syntheses of Sensitizers For Use In Photodynamic Therapy, J. Chem. Soc. Perkin Trans. I, pp. 2369–2377, 1993.

Pandey R. et al., Fast Atom Bombardment Mass Spectral Analyses Of Photofrin II® And Its Synthetic Analogs, Biomedical and Enviromental Mass Spectrometry, vol. 19, pp. 405–414, 1990.

Pandey, R. et al., Chemistry Of Photofrin II And Some New Photosensitizers, SPIE vol. 1065 Photodynamic Therapy: Mechanisms, pp. 164–174, 1989.

Pandey, R. et al., Structure/Activity Relationships Among Photosensitizers Related To Pheophorbides And Bacteriopheophorbides, Bioorganic & Medicinal Chemistry Letters, vol. 2, No. 5, pp. 491–496, 1992.

Pandey, R. et al., Substituent Effects In Tetrapyrrole Subunit Reactivity And Pinacol–Pinacolone Rearrangements: Vic–Dihydroxychlorins And Vic–Dihydroxybacteriochlorins, Tetrahedron Letters, vol. 22, No. 51, pp. 7815–7818, 1992.

Pandey, R. et al., Alkyl Ether Analogs Of Chlorophyll–a Derivatives: Part 1. Synthesis, Photophysical Properties And Photodynamic Efficacy, Photochemistry and Photobiology, 64(1), pp. 194–204, 1996.

Pandey, R. et al., Evaluation Of New Benzoporphyrin Derivatives With Enhanced PDT Efficacy, Photochemistry and Photobiology, vol. 62, No. 4, pp. 764–768, 1995.

Pandey, R. et al., Synthesis Of New Bacteriochlorins And Their Antitumor Activity, Bioorg. and Med. Chem. Letters, 1992.

Weishaupt, K. et al., Identification Of Singlet Oxygen As The Cytotoxic Agent In Photo–Inactivation Of A Murine Tumor, Cancer Research 36, pp. 2326–2329, 1976.

R = Various alkyl, aryl groups, X = O, S or NH, Y = O, S, 2H, Z = H or CH$_3$

FIGURE 1

R = H or X= O, S, NH, R$_1$ = Various alkyl (1-12 carbon units) or aryl groups

R$_2$ = Various alkyl, aryl or amino acids

CAROTENE ANALOGS OF PORPHYRINS, CHLORINS AND BACTERIOCHLORINS AS THERAPEUTIC AND DIAGNOSTIC AGENTS

BACKGROUND OF THE INVENTION

In recent years, the use of fluorescence spectroscopy has been explored for diagnosis of cancer. Infrared imaging (IRI) using a spectroscopic agent, has several advantages over other in vivo techniques in that the technique is non-invasive and under proper conditions can give deep penetration and quantitative results. The complete profile of uptake, retention and elimination of needed spectroscopic agents can be followed within a single laboratory animal thus reducing the number of animals required in preclinical trials.

The requirements for an ideal spectroscopic agent needed for infrared imaging techniques are as follows: i) it should preferentially localize in tumor cells; ii) it should have high fluorescent efficiency; iii) it should not produce phototoxicity or other adverse effects in a patient; iv) it should be easy to synthesize; v) it should be chemically pure; and vi) it should have a long wave length emission so that deep seated tumors can be detected.

Porphyrins, chlorins, and bacteriochlorins including their analogs and derivatives have recently found superior utility as photodynamic compounds for use in diagnosis and treatment of disease, especially certain cancers. These compounds have also found utility in treatment of psoriasis and papillomatosis.

Such derivatives include dimers and trimers of these compounds. Permissible derivatives also include ring variations of these compounds; provided that, the central sixteen sided four nitrogen heterocycle of these compounds remains intact. Chlorophyllins, purpurins and pheophorbides and their derivatives are, therefore, included within "porphyrins, chlorins, and bacteriochlorins and their derivatives and analogs". Such derivatives include modifications of substituents upon these ring structures.

Numerous articles have been written on this subject, e.g. "Use of the Chlorophyll Derivative Purpurin-18, for Synthesis of Sensitizers for Use in Photodynamic Therapy", Lee et al., J. Chem. Soc., 1993, (19) 2369–77; "Synthesis of New Bacteriochlorins And Their Antitumor Activity", Pandey et al., Biology and Med. Chem. Letters, 1992; "Photosensitizing Properties of Bacteriochlorophyllin a and Bacteriochlorin a, Two Derivatives of Bacteriochlorophyll a", Beems et al., Photochemistry and Photobiology, 1987, v. 46, 639–643; "Photoradiation Therapy. II. Cure of Animal Tumors With Hematoporphyrin and Light", Dougherty et al., Journal of the National Cancer Institute, July 1975, v. 55, 115–119; "Photodynamic therapy of C3H mouse mammary carcinoma with haematoporphyrin di-esters as sensitizers", Evensen et al., Br. J. Cancer, 1987, 55, 483–486; "Substituent Effects in Tetrapyrrole Subunit Reactivity and Pinacol-Pinacolone Rearrangements: VIC-Dihydroxychlorins and VIC-Dihydroxybacteriochlorins" Pandey et al., Tetrahedron Letters, 1992, v. 33, 7815–7818; "Photodynamic Sensitizers from Chlorophyll: Purpurin-18 and Chlorin $p_6$", Hoober et al., 1988, v.48, 579–582; "Structure/Activity Relationships Among Photosensitizers Related to Pheophorbides and Bacteriopheophorbides", Pandey et al., Bioorganic and Medicinal Chemistry Letters, 1992, v 2, 491–496; "Photodynamic Therapy Mechanisms", Pandey et al., Proceedings Society of Photo-Optical Instrumentation Engineers (SPIE), 1989, v 1065, 164–174; and "Fast Atom Bombardment Mass Spectral Analyses of Photofrin II® and its Synthetic Analogs", Pandey et al., Biomedical and Environmental Mass Spectrometry, 1990, v. 19, 405–414. These articles are incorporated by reference herein as background art.

Numerous patents in this area have been applied for and granted world wide on these photodynamic compounds. Reference may be had, for example to the following U.S. patents which are incorporated herein by reference: U.S. Pat. Nos. 4,649,151; 4,866,168; 4,889,129; 4,932,934; 4,968,715; 5,002,962; 5,015,463; 5,028,621; 5,145,863; 5,198,460; 5,225,433; 5,314,905; 5,459,159; 5,498,710; and 5,591,847.

At least one of these compounds "Photofrin®" has received approval for use in the United States, Canada and Japan. Others of these compounds are in clinical trials or are being considered for such trials.

The term "porphyrins, chlorins and bacteriochlorins" as used herein is intended to include their derivatives and analogs, as described above, and as described and illustrated by the foregoing articles and patents incorporated herein by reference as background art.

Such compounds have been found to have the remarkable characteristic of preferentially accumulating in tumors rather than most normal cells and organs, excepting the liver and spleen. As a result, many tumors can be detected at an early stage due to the light fluorescing nature of the compounds in the tumors. Furthermore, many such tumors can be killed because the compounds may be activated by light to become tumor toxic.

Unfortunately such compounds, as might be expected, are not without some side affects. One of the most annoying, though usually manageable, side effects is the fact that patients exposed to these compounds become sensitive to light. As a result, after treatment, a patient must restrict exposure to light, especially sun light, by remaining indoors as much as possible, by use of dark glasses and by careful use of sun screens.

It would therefore be desirable to have a photodynamic compound, as described above, which continues to be effective as a diagnostic aid, yet having reduced photosensitizing qualities.

BRIEF DESCRIPTION OF THE INVENTION

In accordance with the invention, photodynamic compounds are provided which continue to have desired photodiagnostic qualities but with reduced photosensitizing characteristics for the patient.

In particular, such compounds have been surprisingly found which are relatively simple derivatives of many known effective photodynamic compounds.

Such compounds are carotene conjugates of photosensitizers selected from the group consisting of porphyrins, chlorins and bacteriochlorins. It was especially surprising that the carotene conjugation does not significantly reduce the tumor uptake characteristics of the photosensitizer.

"Carotene" as used herein means carotene and any slight modification thereof which does not adversely affect the phototoxicity reducing quality, e.g. the singlet oxygen quenching characteristic, of the carotene.

The compounds of the invention can be readily made from essentially any of the porphyrins, chlorins and bacteriochlorins discussed above in background art; provided that, such compound has a free carboxylic acid group or a free carboxylic acid ester group or a free carboxylic acid salt group, (collectively "carboxy functionality"). Most of the porphyrins, chlorins, and bacteriochlorins discussed in the background of the invention have such a group.

In preparing the compounds of the invention, the carboxy functionality is activated by reaction with a suitable carotene reactive substance and then reacted with the carotene. For example, the carboxy functionality may be reacted with a carbodiimide and then condensed with amino carotene to obtain the desired carotene conjugate.

A generic formula for many such carotene conjugates is:

where $R^1$ is hydrogen or methyl; $R^2$ is:

$R^3$, $R^4$ and $R^5$ are independently, hydrogen, methyl or ethyl; $R^6$ and $R^7$ are independently —$R^3$, —$OR^{13}$, —$C(R^{16})(O)$, —$C(R^{16})_2OR^-$, —CH=$CHR^{13}$, or —$(CH_2)R^{14}$; $R^8$ is —$R^{13}$, —$OR^{13}$, —$C(R^{16})(O)$, —$C(R^{16})_2OR^{13}$, —CH=$CHR^{13}$, or —$(CH_2)R^{14}$ or taken with $R^{10}$ is =O; $R^9$ is —$R^{13}$, —$OR^{13}$, —$C(R^{16})(O)$, —$C(R^{16})_2OR^{13}$, —CH=$CHR^{13}$, or —$(CH_2)R^{14}$ or taken with $R^{10}$ is a chemical bond; $R^{10}$ is —$R^{13}$, —$OR^{13}$, —$C(R^{16})(O)$, —$C(R^{16})_2OR^{13}$, —CH=$CHR^{13}$, or —$(CH_2)R^{14}$ or taken together with $R^9$ is a chemical bond or taken with $R^8$ is =O; $R^{11}$ is $R^{13}$, or —$OR^{13}$; $R^{12}$ is —$C(R^{13})_2C(Y)$—, —$C(O)O(O)C$—, —$C(NR^{13})O(O)C$—, or —$C(O)N(R^{15})$—$C(O)$—;

$R^{13}$ is, independently at each occurrence, hydrogen or lower alkyl of from 1 through about 10 carbon atoms; $R^{14}$ is an amino acid residue, $R^{15}$ is —$R^{13}$, —$R^{14}$, or —$C(O)NHR^{13}$; $R^{16}$ is, independently at each occurrence, hydrogen or lower alkyl of 1 to about 4 carbon atoms and Y is =O, =S, or 2H—.

DETAILED DESCRIPTION OF THE INVENTION

Specific embodiments illustrating the compounds of the invention are as follows:

1. $R^1$ is H, $R^3$ is —$CH_3$, $R^4$ is H, $R^5$ is $CH_3$, $R^6$ is —$CH(CH_3)O(CH_2)_6CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)CH_2$—.

2. $R^1$ is H, $R^3$ is —$CH_3$, $R^4$ is H, $R^5$ is $CH_3$, $R^6$ is —$CH(CH_3)O(CH_2)_6CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_3CH_3)CH_3$—.

3. $R^1$ is H, $R^3$ is —$CH_3$, $R^4$ is H, $R^5$ is —$CH_3$, $R^6$ is —$CH(CH_3)O(CH_2)_6CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_3CH_3)CH_3$—.

4. $R^1$ is H, $R^3$ is —$CH_3$, $R^4$ is H, $R^5$ is —$CH_3$, $R^6$ is —$CH(CH_3)OCH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_2CH_3)C(O)$—.

5. $R^1$ is H, $R^3$ is —$CH_3$, $R^4$ is H, $R^5$ is —$CH_3$, $R^6$ is —$CH(CH_3)O(CH_2)_2CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_2CH_3)C(O)$—.

6. $R^1$ is H, $R^3$ is —$CH_3$, $R^4$ is H, $R^5$ is $CH_3$, $R^6$ is —$CH(CH_3)OCH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5CH_3)C(O)$—.

7. $R^1$ is H, $R^3$ is —$CH_3$, $R^4$ is H, $R^5$ is $CH_3$, $R^6$ is —$CH(CH_3)O(CH_2)_2CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5CH_3)C(O)$—.

8. $R^1$ is H, $R^3$ is —$CH_3$, $R^4$ is H, $R^5$ is $CH_3$, $R^6$ is —$CH(CH_3)O(CH_2)_5CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5CH_3)C(O)$—.

9. $R^1$ is H, $R^3$ is —$CH_3$, $R^4$ is H, $R^5$ is $CH_3$, $R^6$ is —$CH(CH_3)O(CH_2)_5CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5CH_3)C(O)$—.

10. $R^1$ is H, $R^3$ is —$CH_3$, $R^4$ is H, $R^5$ is $CH_3$, $R^6$ is —$CH_2CH_2OR^{17}$, $R^7$ is —$CH_3$, $R^8$ is —$CH_2CH_3$, $R^9$ and $R^{10}$ together form a chemical bond, $R^{11}$ is —$CH_3$ and R is —$C(O)N((CH_2)_5CH_3)C(O)$— and $R^{17}$ is primary or secondary alkyl containing 1 to about 20 carbon atoms.

11. $R^1$ is H, $R^3$ is —$CH_3$, $R^4$ is H, $R^5$ is —$CH_3$, $R^6$ is —$CH(CH_3)OR^{17}$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5CH_3)C(O)$— and $R^{17}$ is primary or secondary alkyl containing 1 to about 20 carbon atoms.

12. $R^1$ is H, $R^3$ is —$CH_3$, $R^4$ is H, $R^5$ is $CH_3$, $R^6$ is lower alkyl of 1 to 4 carbon atoms or a formal or carbonyl containing group of 1 to 4 carbon atoms, $R^7$ is —$CH_3$, $R^8$ is H, —$OR^{13}$ or with $R^{10}$ is =O, $R^9$ is H, —$OR^{13}$ or with $R^{10}$ forms a chemical bond, $R^{10}$ is ethyl or with $R^9$ forms a chemical bond or with $R^8$ is =O, $R^{11}$ is —$CH_3$ and $R^{12}$ is —$C(O)N(R^{13})C(O)$— or —$C(O)O(O)C$—.

13. $R^1$ is hydrogen, $R^3$ is methyl, $R^4$ is hydrogen, $R^5$ is methyl, $R^6$ is —$CH(CH_3)OR^{13}$, $R^7$ is methyl, $R^8$ is ethyl, $R^9$ and $R^{10}$ together form a chemical bond; $R^{11}$ is methyl; and $R^{12}$ is —$CH_2C(O)$—.

14. $R^1$ is hydrogen, $R^3$ is methyl, $R^4$ is hydrogen, $R^5$ is methyl, $R^6$ is —CH=$CH_2$, $R^7$ is methyl, $R^8$ is ethyl, $R^9$ and $R^{10}$ together form a chemical bond; $R^{11}$ is methyl; and $R^{12}$ is —$CH_2C(O)$—.

15. $R^1$ is hydrogen, $R^3$ is methyl, $R^4$ is hydrogen, $R^5$ is methyl, $R^6$ is —$CH(CH_3)O(CH_2)_5CH_3$, $R^7$ is methyl, $R^8$ is ethyl, $R^9$ and $R^{10}$ together form a chemical bond; $R^{11}$ is methyl; and $R^{12}$ is —$CH_2C(O)$—.

16. $R^1$ is hydrogen, $R^3$ is methyl, $R^4$ is hydrogen, $R^5$ is methyl, $R^6$ is —CH=$CH_2$, $R^7$ is methyl, $R^8$ is ethyl, $R^9$ and $R^{10}$ together form a chemical bond; $R^{11}$ is methyl; and $R^{12}$ is —$C(O)OC(NR^{13})$—.

17. $R^1$ is hydrogen, $R^3$ is methyl, $R^4$ is hydrogen, $R^5$ is methyl, $R^6$ is —CH=$CH_2$, $R^7$ is methyl, $R^8$ is ethyl, $R^9$ and $R^{10}$ are hydrogen; $R^{11}$ is methyl; and $R^{12}$ is —$C(O)OC(NR^{13})$—.

Preferred compounds of the invention may be represented by the following formulas:

1.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^9$ together contain no more than a total of 16 carbon atoms.

2.

Where $R^6$, $R^7$, and $R^8$ are independently hydrogen, alkyl, alkoxy, formyl, ketyl, alkenyl, alkylene alkyl ether or an amino acid residue; provided that, $R^6$, $R^7$, and $R^8$ together contain no more than a total of 16 carbon atoms.

3.

Where $R^6$, $R^7$, and $R^8$ are independently hydrogen, alkyl, alkoxy, formyl, ketyl, alkenyl, alkylene alkyl ether or an amino acid residue; provided that, $R^6$, $R^7$, and $R^8$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

4.

Where $R^6$, $R^7$, and $R^8$ are independently hydrogen, alkyl, alkoxy, formyl, ketyl, alkenyl, alkylene alkyl ether or an amino acid residue; provided that, $R^6$, $R^7$, and $R^8$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

5.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^8$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^9$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

6.

7.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^9$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^9$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

8.

9.

Where $R^6$, $R^7$, and $R^8$ are independently hydrogen, alkyl, alkoxy, formyl, ketyl, alkenyl, alkylene alkyl ether or an amino acid residue; provided that, $R^6$, $R^7$, and $R^8$ together contain no more than a total of 16 carbon atoms and $R^{15}$ is hydrogen, alkyl, alkoxy, formyl, ketyl, alkenyl, alkylene alkyl ether, an amino acid residue or —C(O)NHR$^{18}$ where $R^{18}$ is lower alkyl of from 1 to about 12 carbon atoms.

10.

Where $R^6$, $R^7$, and $R^9$ are independently hydrogen, alkyl, alkoxy, formyl, ketyl, alkenyl, alkylene alkyl ether or an amino acid residue; provided that, $R^6$, $R^7$, and $R^9$ together contain no more than a total of 16 carbon atoms.

Many photosensitizers, suitable as starting materials in accordance with the present invention for combination with carotene, have the formula:

where $R^1$ is hydrogen or methyl; $R^2$ is —OH; $R^3$, $R^4$ and $R^5$ are independently, hydrogen, methyl or ethyl; $R^6$ and $R^7$ are independently —$R^{13}$, —$OR^{13}$, —$C(R^{16})(O)$, —$C(R^{16})_2 OR^{13}$, —CH═$CHR^{13}$, or $(CH_2)R^{14}$; $R^8$ is —$R^{13}$, —$OR^{13}$, —$C(R^{16})(O)$, —$C(R^{16})_2 OR^{13}$, —CH═$CHR^{13}$, or —$(CH_2)R^{14}$ or taken with $R^{10}$ is ═O; $R^9$ is —$R^{13}$, —$OR^{13}$, —$C(R^{16})(O)$, —$C(R^{16})_2 OR^{13}$, —CH═$CHR^{13}$, or —$(CH_2)R^{14}$ or taken with $R^{10}$ is a chemical bond; $R^{10}$ is —$R^{13}$, —$OR^{13}$, —$C(R^{16})(O)$, —$C(R^{16})_2 OR^{13}$, —CH═$CHR^{13}$, or —$(CH_2)R^{14}$ or taken together with $R^9$ is a chemical bond or taken with $R^8$ is ═O; $R^{11}$ is $R^{13}$, or —$OR^{13}$; $R^{12}$ is —$C(R^{13})_2 C(Y)$—, —C(O)O(O)C—, —$C(NR^{13})O(O)C$—, or —$C(O)N(R^{15})$—C(O)—; $R^{13}$ is, independently at each occurrence, hydrogen or lower alkyl of from 1 through about 10 carbon atoms; $R^{14}$ is an amino acid residue, $R^{15}$ is —$R^{13}$, —$R^{14}$, or —$C(O)NHR^{13}$; $R^{16}$ is, independently at each occurrence, hydrogen or lower alkyl of 1 to about 4 carbon atoms and Y is ═O, ═S, or 2H—.

HPPH, formula 9 above where $R^6$ is —$C(CH_3)$O-hexyl, $R^7$ is —$CH_3$, $R^8$ is —$CH_2CH_3$ and the position of the carotene structure is substituted with —COOH, described in U.S. Pat. No. 5,198,460 is reacted with amino carotene to form a carotene conjugate in accordance with the invention, as described below: Formula references are to those shown in the drawings.

The carboxylic acid functionality was first activated by preparing carbodiimide analog (in situ) before condensing with amino carotene. The structure of the conjugate was confirmed by NMR and mass spectrometry. The singlet oxygen production by HPPH and its carotene conjugate was measured in oxygen saturated toluene solutions by monitoring the singlet oxygen phosphorescence at 1270 nm. Ample production of singles oxygen was detected in case of HPPH [singles oxygen yield ($\Phi_A$)=0.45 and fluorescence yield ($\Phi_f$)=0.48].[5] Under similar experimental conditions, the carotene conjugate did not produce singlet oxygen. Thus, a complete photoprotection was achieved.

Figure 1:
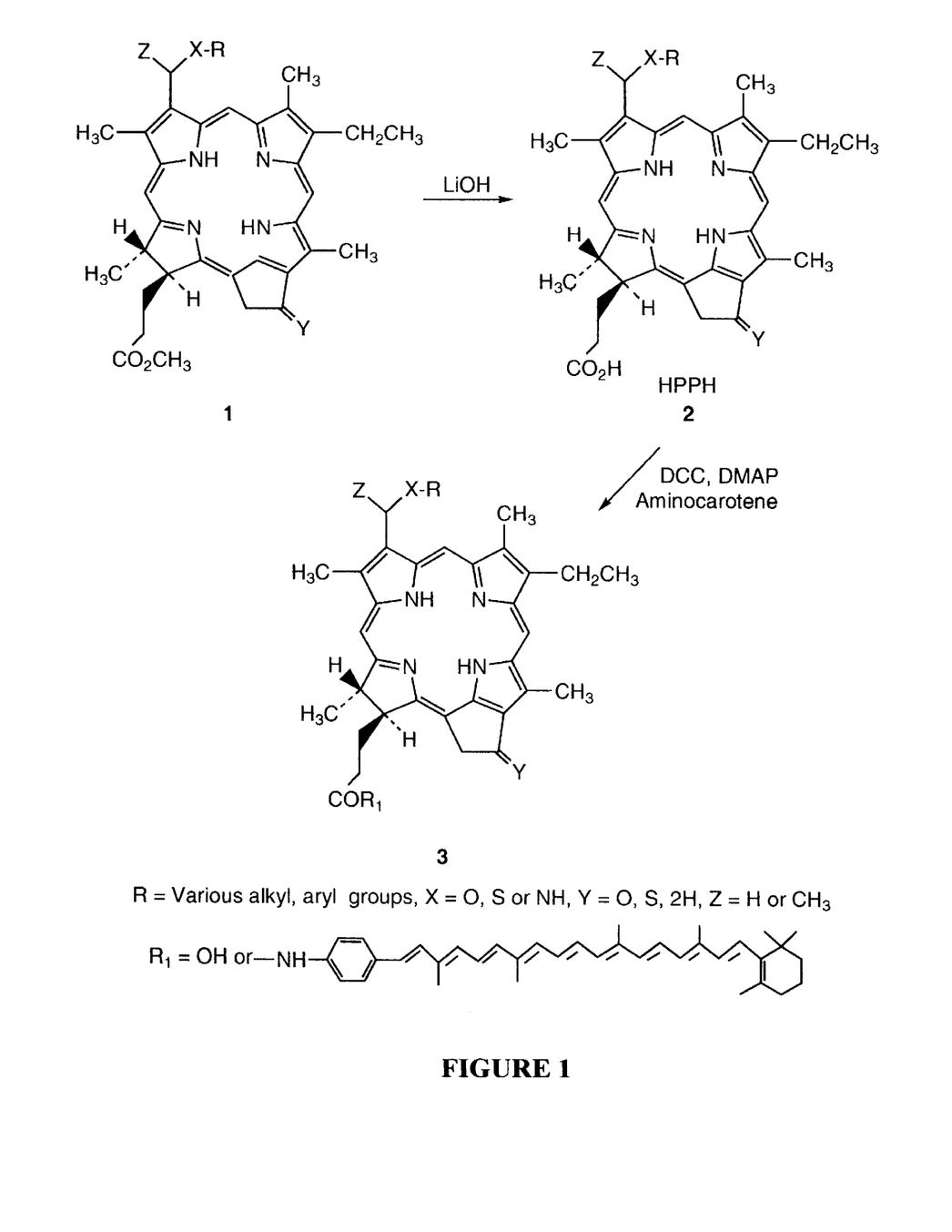
FIG. 1 shows a schematic reaction scheme for preparation of HPPH-carotene conjugate from HPPH and aminocarotene.
Figure 2:
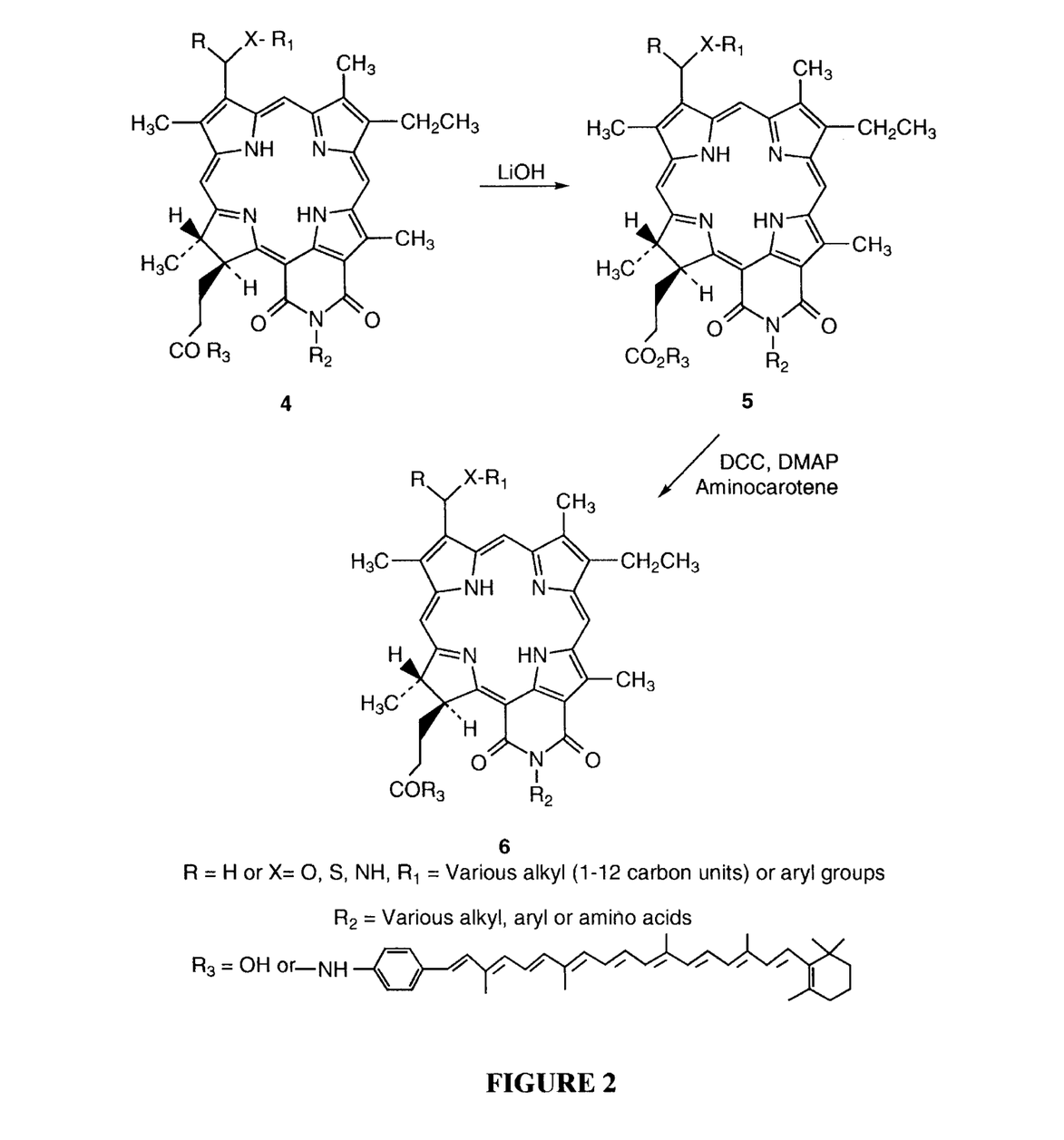
FIG. 2 shows a schematic reaction scheme for preparation of purpurin imide-carotene conjugate from purpurine imide and aminocarotene.

Determination of Tumor Uptake by In Vivo Reflection Spectroscopy:

The tumor uptake of the parent photosensitizer 2 (HPPH), FIG. 1, and purpurin with a fused imide ring 4, FIG. 2, were compared to the corresponding carotene conjugate 3 and 6 by in vivo reflection spectroscopy.

Figure 3:
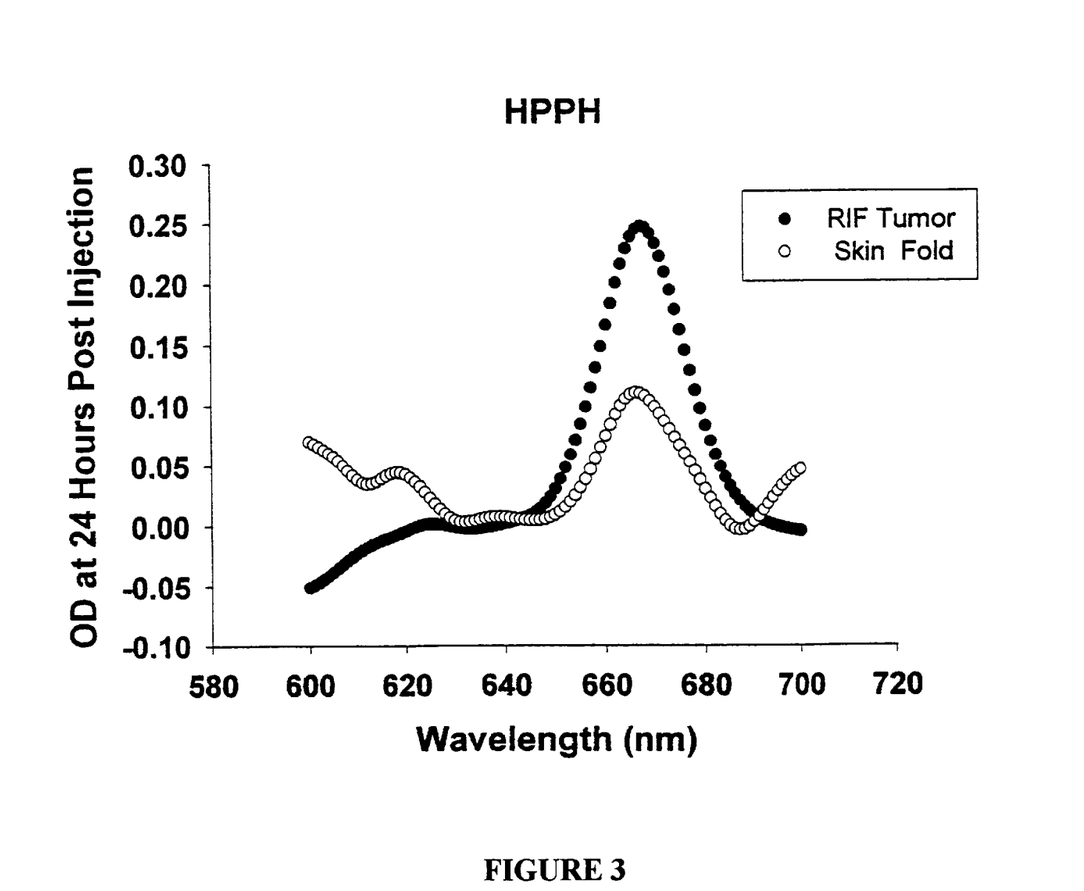
FIG. 3 is a graph showing uptake of HPPH at 24 hours post injection.
Figure 4:
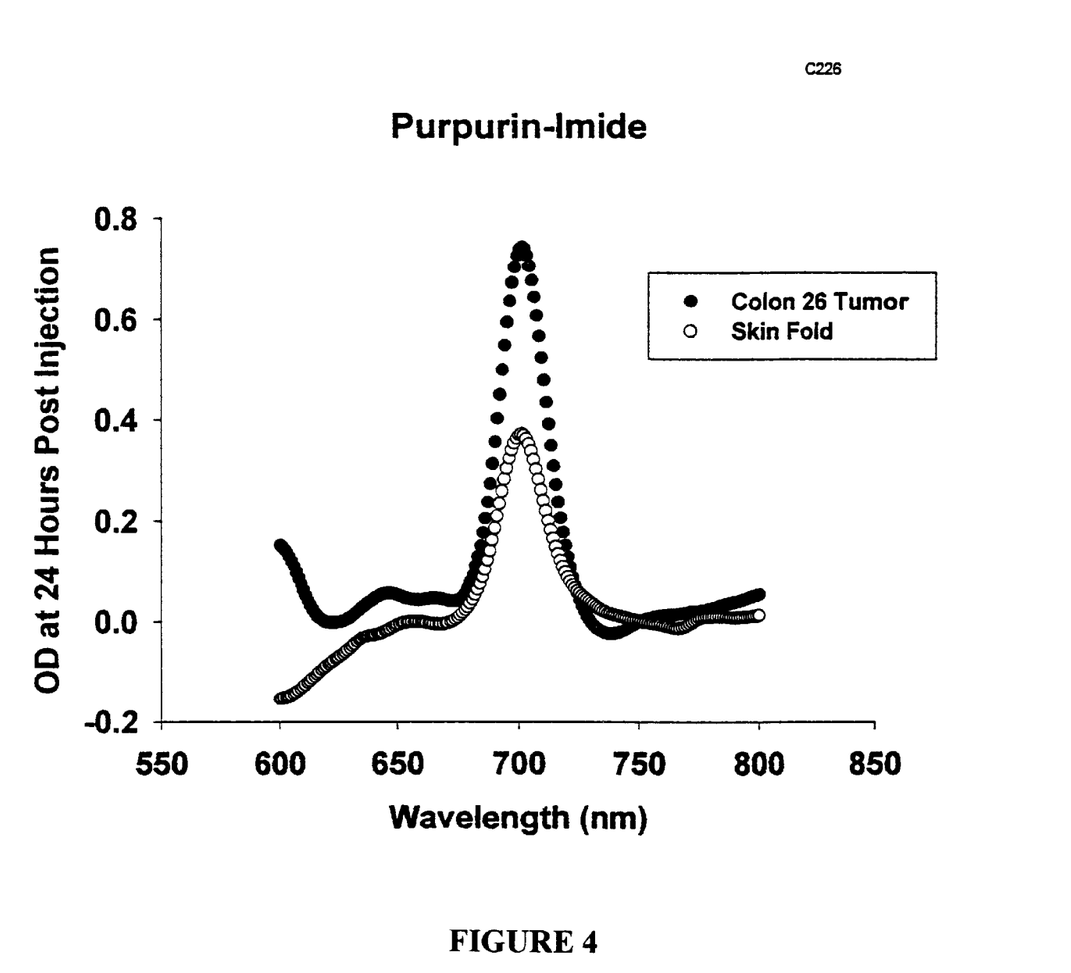
FIG. 4 is a graph showing uptake of purpurin imide at 24 hours post injection.
Figure 5:
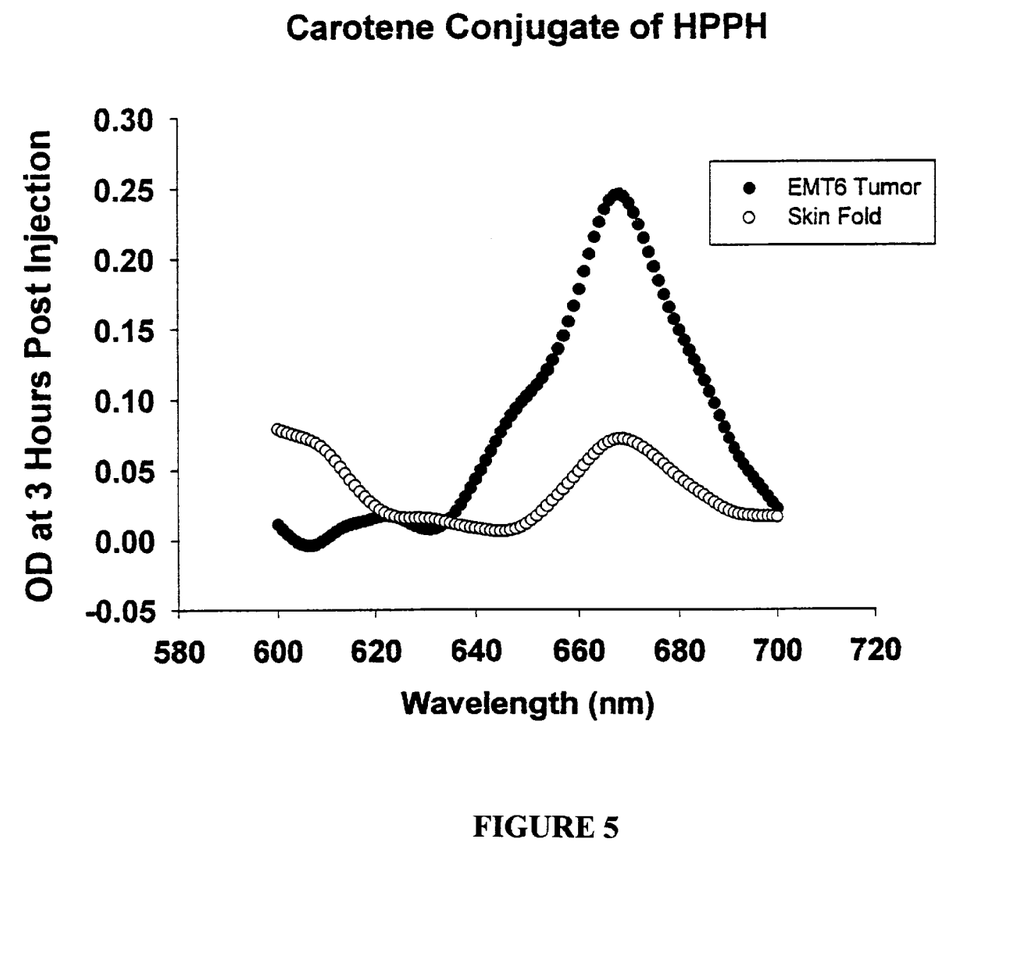
FIG. 5 is a graph showing uptake of HPPH-carotene conjugate at 3 hours post injection.
Figure 6:
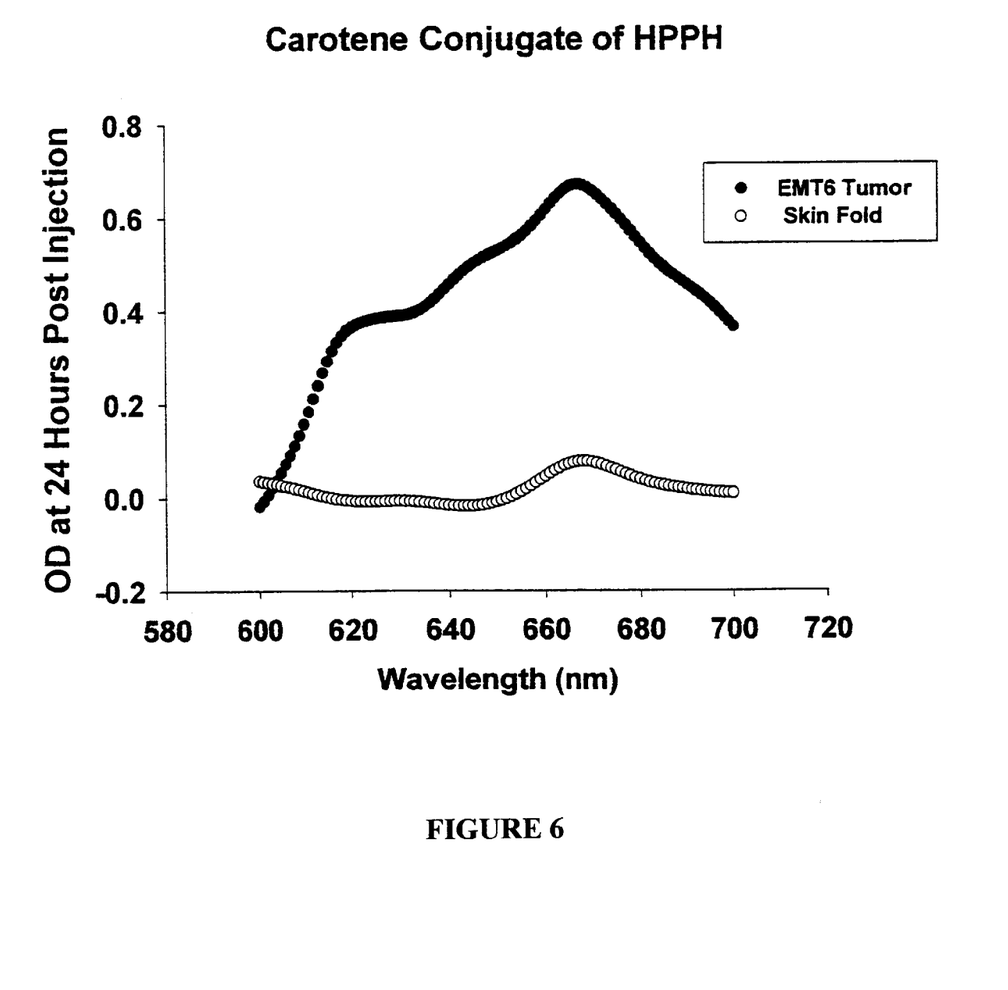
FIG. 6 is a graph showing uptake of HPPH-carotene conjugate at 24 hours post injection.

For these experiments, C3H mice with an axillary radiation induced fibrosarcoma (RIF) tumor were injected with the drug in an amount of 5 micro mole/Kg of body weight and the in vivo absorption specta were taken at various time intervals. FIGS. 3 and 4 respectively show the uptake of HPPH 2 and purpurin-imide 4 at 24 h post injection. FIGS. 5 and 6 show the uptake of the HPPH-carotene conjugate at 3 h and 24 h post injection. Compared to parent compound (HPPH, FIG. 3), the corresponding carotene conjugate shows a significant uptake of the drug in the tumor vs the skin fold. Similar enhancement in tumor uptake was observed with carotene conjugate of purpurin imide 6 as compared with the parent analog 4.

Preliminary In Vivo Activity:

RIF rumors were implanted subcutaneously into the axilla of 5–7 week old female C3H mice. When tumors grew to about 5 mm diameter, mice were injected with photosensitizers at various doses. The mice (6 mice/group) were restrained in aluminum holders and each tumor illuminated with 135 J/cm² light from a laser tuned at the longest wavelength absorption maximum of the photosensitizers. The percentage of short-term control was recorded daily.

(A) Alkyl Ether Analogs of Purpurin-18 Imides:

The preliminary in vivo activity of some of the compounds are summarized in Table 1. These data indicated that: (1) the hydrophobicity of the molecule can be varied by changing the length of the carbon chain (N-alkyl or -alkyl substituents), (ii) in some cases, compounds with same hydrophobic characteristics (same log p values), did not show similar activity; (iii) thus besides hydrophobicity, the steric and electronic factors also play important role in designing effective photosensitizers.

Among the compounds tested, the heptyl ether derivative of purpurin imide bearing N-hexyl substituent was found to be most effective at a dose of 1.0 $\mu$mol/kg. The treatment and dose conditions for all the photosensitizers are briefly discussed in Table 1.

(B) Comparative In Vivo Activity of Photosensitizers with and without Carotene:

The in vivo photosensitizing activity of HPPH 2, and purpurin-imide 4 was compared with their corresponding carotene analogs, and the results are summarized in Table 2. As expected, compared to the non-carotenoid photosensitizers, carotene-conjugated photosensitizers were found to be ineffective. This is possibly due to the carotene scavenging of singlet oxygen. Singlet oxygen is usually a necessary requirement for an effective photosensitizer.

Fluorescence Spectroscopy:

The fluorescence spectra of HPPH 2, purpurin-imide 4 and their corresponding carotene conjugates 3 and 6 were measured in dichloromethane. In the case of HPPH and its carotenoid analog, excitation at 660 nm gave strong emission at 670 nm. Similarly, purpurin imide and its carotenoid analog on excitation at 705 nm produced emission at 715 nm. Due to their strong fluorescence, and higher uptake in tumors, these compounds show great potential for use as diagnostic agents for malignant and non-malignant tumors.

Synthesis and Characterization of Carotene Conjugates:

HPPH-Carotene Conjugate:

Hexyl ether analog of pyropheophorbide-a 2 was prepared by following the method reported previously (Pandey and Dougherty, U.S. Pat. No. 5,198,460). Amino carotene (obtained from Mallinckrodt Medical Inc., St. Louis) was added into a solution of HPPH in dichloromethane containing a catalytic amount of dimethylaminopyridine (DMAP). The reaction mixture was stirred overnight. The solvent was evaporated, and the desired product was obtained by chromatography (Alumina/eluting with dichloromethane). Yield 65%. The structure of the conjugate was confirmed by NMR and mass spectrometry. See FIG. 1.

Purpurin Imide-Carotene Conjugate:

Methylpheophorbide-a was isolated from the alga *Spirulina pacifica*, and reacted with alkyl amines. The intermediate amides as carboxylic acid analogs were converted to the corresponding methyl esters, which on stirring with methanolic KOH at room temperature (5–10 min) produced the N-alkyl imide derivatives in 65–70% yield. The vinyl groups were then converted to various alkyl ether analogs by first reacting with 30% HBr/AcOH, and then with the desired alcohol (for example 4, FIG. 2). The desired non-carotene conjugate analogs (Table 1) were prepared in high yield (70–75%). The methyl ester group (e.g., heptyl ether analog of N-hexyl purpurin imide 4) was hydrolyzed to the corresponding carboxylic acid, which was then converted into the respective carotene derivative by following the method discussed for the related HPPH-carotene conjugate. The structure of the conjugate was confirmed by NMR and mass spectrometry. The reaction sequences for the preparation of carotenoid analog 6 is shown in FIG. 2.

HPPH and purpurine imide were used as being typical of the many carboxy containing porphyrin, chlorin and bacteriochlorin photosensitizers described in the background art. All of such photosensitizers are expected to form carotene conjugates in a manner similar to HPPH and purpurin imide.

Carotene conjugates of the invention are clearly useful in fluorescence spectroscopy for diagnosis of cancer without the photosensitizing characteristics of the base compounds.

TABLE 1

Preliminary in vivo Activity of Alkyl Ether Analogs of Purpurin-18 imides

| $R_1$ | R | Partition Coefficient (log P) | Tumor Response (%) [days]* | | | | | |
|---|---|---|---|---|---|---|---|---|
| | | | 1–2 | 7 | 14 | 21 | 30 | 90 |
| Methyl | Propyl | 6.22 | | | NR | | | |
| Propyl | Propyl | 7.22 | 100 | 33 | 17 | ongoing | | |
| Methyl | Hexyl | 7.72 | | | NR | | | |
| Propyl | Hexyl (0.5 μmol)* | 8.72 | | | NR | | | |
| Hexyl | Propyl (0.5 μmol)* | 8.72 | 100 | 66 | 33 | 17 | 17 | 17 |
| Hexyl | Propyl | 8.72 | 100 | 83 | 83 | 50 | 33 | 33 |
| Heptyl | Hexyl (0.25 μmol)* | 10.72 | 100 | 60 | 20 | 20 | 20 | 20 |
| Heptyl | Hexyl | 10.72 | 100 | 100 | 100 | 100 | 100 | 83 |

*Six mice/group (RIF tumor). 1.0 μmol/kg, 705 nm, 135 J/cm² (24 h post injection).

TABLE 2

Preliminary In vivo Activity of Photosensitizers With And Without Carotene

| Compound | Dose (μmol/kg) | Time between inj. & treatment | Wavelength (nm) (for treatment) | % TUMOR RESPONSE (day)* | | | | |
|---|---|---|---|---|---|---|---|---|
| | | | | 1–2 | 7 | 21 | 30 | 90 |
| HPPH (2) | 0.47 | 24 | 665 | 100 | 100 | 80 | 50 | 50 |
| HPPH-carotene (3) | 0.47 | 24 | 665 | NO RESPONSE | | | | |
| Purpurin-imide (4) | 1.0 | 24 | 705 | 100 | 100 | 100 | 100 | 83¶ |
| Purpurin-imide-carotene (6) | 1.0 | 24 | 705 | NO RESPONSE | | | | |

*Six mice/group (RIF tumor). 135 J/cm²
¶5/6 mice were tumor free on day 90.

What is claimed is:

1. A carotene conjugate of a photosensitizer selected from the group consisting of porphyrins, chlorins and bacteriochlorins, said conjugation occurring at a pyrrolic position of the porphyrin, chlorin or bacteriochlorin, wherein the conjugated photosensitizer can be excited at a wave length of at least about 660 nm to give a detectable emission at a wave length of at least about 670 nm, said conjugated photosensitizer having at least one detectable emission wave length at least 10 nm longer than the exciting wave length.

2. A photosensitizer of claim 1 of the formula:

where $R^1$ is hydrogen or methyl; $R^2$ is:

$R^3$, $R^4$ and $R^5$ are independently, hydrogen, methyl or ethyl; $R^6$ and $R^7$ are independently —$R^{13}$, —$OR^{13}$, —$C(R^{16})(O)$, —$C(R^{16})_2 OR^{13}$, —$CH=CHR^{13}$, or —$(CH_2)R^{14}$; $R^8$ is —$R^{13}$, —$OR^{13}$, —$C(R^{16})(O)$, —$C(R^{16})_2 OR^{13}$, —$CH=CHR^{13}$, or —$(CH_2)R^{14}$ or taken with $R^{10}$ is =O; $R^9$ is —$R^{13}$, —$OR^{13}$, —$C(R^{16})(O)$, —$C(R^{16})_2 OR^{13}$, —$CH=CHR^{13}$, or —$(CH_2)R^{14}$ or taken with $R^{10}$ is a chemical bond; $R^{10}$ is —$R^{13}$, —$OR^{13}$, —$C(R^{16})(O)$, —$C(R^{16})_2 OR^{13}$, —$CH=CHR^{13}$, or —$(CH_2)R^{14}$ or taken together with $R^9$ is a chemical bond or taken with $R^8$ is =O; $R^{11}$ is $R^{13}$, or —$OR^{13}$; $R^{12}$ is —$C(R^{13})_2 C(Y)$—, —$C(O)O(O)C$—, —$C(NR^{13})O(O)C$—, or —$C(O)N(R^{15})$—$C(O)$—; $R^{13}$ is, independently at each occurrence, hydrogen or lower alkyl of from 1 through about 10 carbon atoms; $R^{14}$ is an amino acid residue, $R^{15}$ is —$R^{13}$, —$R^{14}$, or —$C(O)NHR^{13}$; $R^{16}$ is, independently at each occurrence, hydrogen or lower alkyl of 1 to about 4 carbon atoms and Y is =O, =S, or 2H—.

3. The compound of claim 2 wherein. $R^1$ is H, $R^3$ is —$CH_3$, $R^4$ is H, $R^5$ is $CH_3$, $R^6$ is —$CH(CH_3)O(CH_2)_6 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)CH_2$—.

4. The compound of claim 2 wherein $R^1$ is H, $R^3$ is —$CH_3$, $R^4$ is H, $R^5$ is $CH_3$, $R^6$ is —$CH(CH_3)O(CH_2)_6 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5 CH_3)CH_3$—.

5. The compound of claim 2 wherein $R^1$ is H, $R^3$ is —$CH_3$, $R^4$ is H, $R^5$ is $CH_3$, $R^6$ is —$CH(CH_3)O(CH_2)_6 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_3 CH_3)CH_3$—.

6. The compound of claim 2 wherein $R^1$ is H, $R^3$ is —$CH_3$, $R^4$ is H, $R^5$ is $CH_3$, $R^6$ is —$CH(CH_3)OCH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_2 CH_3)C(O)$—.

7. The compound of claim 2 wherein $R^1$ is H, $R^3$ is —$CH_3$, $R^4$ is H, $R^5$ is $CH_3$, $R^6$ is —$CH(CH_3)O(CH_2)_2 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_2 CH_3)C(O)$—.

8. The compound of claim 2 wherein $R^1$ is H, $R^3$ is —$CH_3$, $R^4$ is H, $R^5$ is $CH_3$, $R^6$ is —$CH(CH_3)OCH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5 CH_3)C(O)$—.

9. The compound of claim 2 wherein $R^1$ is H, $R^3$ is —$CH_3$, $R^4$ is H, $R^5$ is $CH_3$, $R^6$ is —$CH(CH_3)O(CH_2)_2 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$(O)N((CH_2)_5 CH_3)C(O)$—.

10. The compound of claim 2 wherein $R^1$ is H, $R^3$ is —$CH_3$, $R^4$ is H, $R^5$ is $CH_3$, $R^6$ is —$CH(CH_3)O(CH_2)_5 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$(O)N((CH_2)_2 CH_3)C(O)$—.

11. The compound of claim 2 wherein $R^1$ is H, $R^3$ is —$CH_3$, $R^4$ is H, $R^5$ is $CH_3$, $R^6$ is —$CH(CH_3)O(CH_2)_5 CH_3$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5 CH_3)C(O)$—.

12. The compound of claim 2 wherein $R^1$ is H, $R^3$ is —$CH_3$, $R^4$ is H, $R^5$ is $CH_3$, $R^6$ is —$CH_2 CH_2 OR^{17}$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5 CH_3)C(O)$— and $R^{17}$ is primary or secondary alkyl containing 1 to about 20 carbon atoms.

13. The compound of claim 2 wherein $R^1$ is H, $R^3$ is —$CH_3$, $R^4$ is H, $R^5$ is —$CH_3$, $R^6$ is —$CH(CH_3)OR^{17}$, $R^7$ is —$CH_3$, $R^8$ is —$CH_2CH_3$, $R^9$ and $R^{10}$ together form a chemical bond, $R^{11}$ is —$CH_3$ and $R^{12}$ is —$C(O)N((CH_2)_5 CH_3)C(O)$— and $R^{17}$ is primary or secondary alkyl containing 1 to about 20 carbon atoms.

14. The compound of claim 2 wherein $R^1$ is H, $R^3$ is —$CH_3$, $R^4$ is H, $R^5$ is $CH_3$, $R^6$ is lower alkyl of 1 to 4 carbon atoms or a formal or carbonyl containing group of 1 to 4 carbon atoms, $R^7$ is —$CH_3$, , $R^8$ is H, —$OR^{13}$ or with $R^{10}$ is =O, $R^9$ is H, —$OR^{13}$ or with $R^{10}$ forms a chemical bond, $R^{10}$ is ethyl or with $R^9$ forms a chemical bond or with $R^8$ is =O, $R^{11}$ is —$CH_3$ and $R^{12}$ is —$C(O)N(R^{13})C(O)$— or —$C(O)O(O)C$—.

15. The compound of claim 2 wherein $R^1$ is hydrogen, $R^3$ is methyl, $R^4$ is hydrogen, $R^5$ is methyl, $R^6$ is —$CH(CH_3)OR^{13}$, $R^7$ is methyl, $R^8$ is ethyl, $R^9$ and $R^{10}$ together form a chemical bond; $R^{11}$ is methyl; and $R^{12}$ is —$CH_2 C(O)$—.

16. The compound of claim 2 wherein $R^1$ is hydrogen, $R^3$ is methyl, $R^4$ is hydrogen, $R^5$ is methyl, $R^6$ is —$CH=CH_2$, $R^7$ is methyl, $R^8$ is ethyl, $R^9$ and $R^{10}$ together form a chemical bond; $R^{11}$ is methyl; and $R^{12}$ is —$CH_2 C(O)$—.

17. The compound of claim 2 wherein $R^1$ is hydrogen, $R^3$ is methyl, $R^4$ is hydrogen, $R^5$ is methyl, $R^6$ is —$CH(CH_3)O(CH_2)_5 CH_3$, $R^7$ is methyl, $R^8$ is ethyl, $R^9$ and $R^{10}$ together form a chemical bond; $R^{11}$ is methyl; and $R^{12}$ is —$CH_2 C(O)$—.

18. The compound of claim 2 wherein $R^1$ is hydrogen, $R^3$ is methyl, $R^4$ is hydrogen, $R^5$ is methyl, $R^6$ is —CH=CH$_2$, $R^7$ is methyl, $R^8$ is ethyl, $R^9$ and $R^{10}$ together form a chemical bond; $R^{11}$ is methyl; and $R^{12}$ is —C(O)OC(NR$^{13}$)—.

19. The compound of claim 2 wherein $R^1$ is hydrogen, $R^3$ is methyl, $R^4$ is hydrogen, $R^5$ is methyl, $R^6$ is —CH=CH$_2$, $R^7$ is methyl, $R^8$ is ethyl, $R^9$ and $R^{10}$ are hydrogen; $R^{11}$ is methyl; and $R^{12}$ is —C(O)OC(NR$^{13}$)—.

20. A method for diagnosis of cancer which comprises injecting a compound of claim 1 into an animal at a dosage of between 1 and 10 micromoles per kilogram of body weight of the animal and detecting locations of concentrated uptake of said compound by means of spectroscopy.

21. A method for diagnosis of cancer which comprises injecting a compound of claim 2 into an animal at a dosage of between 1 and 10 micromoles per kilogram of body weight of the animal and detecting locations of concentrated uptake of said compound by means of spectroscopy.

22. A method for diagnosis of cancer which comprises injecting a compound of claim 3 into an animal at a dosage of between 1 and 10 micromoles per kilogram of body weight of the animal and detecting locations of concentrated uptake of said compound by means of spectroscopy.

23. A method for diagnosis of cancer which comprises injecting a compound of claim 4 into an animal at a dosage of between 1 and 10 micromoles per kilogram of body weight of the animal and detecting locations of concentrated uptake of said compound by means of spectroscopy.

24. A method for diagnosis of cancer which comprises injecting a compound of claim 5 into an animal at a dosage of between 1 and 10 micromoles per kilogram of body weight of the animal and detecting locations of concentrated uptake of said compound by means of spectroscopy.

25. A method for diagnosis of cancer which comprises injecting a compound of claim 6 into an animal at a dosage of between 1 and 10 micromoles per kilogram of body weight of the animal and detecting locations of concentrated uptake of said compound by means of spectroscopy.

26. A method for diagnosis of cancer which comprises injecting a compound of claim 7 into an animal at a dosage of between 1 and 10 micromoles per kilogram of body weight of the animal and detecting locations of concentrated uptake of said compound by means of spectroscopy.

27. A method for diagnosis of cancer which comprises injecting a compound of claim 8 into an animal at a dosage of between 1 and 10 micromoles per kilogram of body weight of the animal and detecting locations of concentrated uptake of said compound by means of spectroscopy.

28. A method for diagnosis of cancer which comprises injecting a compound of claim 9 into an animal at a dosage of between 1 and 10 micromoles per kilogram of body weight of the animal and detecting locations of concentrated uptake of said compound by means of spectroscopy.

29. A method for diagnosis of cancer which comprises injecting a compound of claim 10 into an animal at a dosage of between 1 and 10 micromoles per kilogram of body weight of the animal and detecting locations of concentrated uptake of said compound by means of spectroscopy.

30. A method for diagnosis of cancer which comprises injecting a compound of claim 11 into an animal at a dosage of between 1 and 10 micromoles per kilogram of body weight of the animal and detecting locations of concentrated uptake of said compound by means of spectroscopy.

31. A method for diagnosis of cancer which comprises injecting a compound of claim 12 into an animal at a dosage of between 1 and 10 micromoles per kilogram of body weight of the animal and detecting locations of concentrated uptake of said compound by means of spectroscopy.

32. A method for diagnosis of cancer which comprises injecting a compound of claim 13 into an animal at a dosage of between 1 and 10 micromoles per kilogram of body weight of the animal and detecting locations of concentrated uptake of said compound by means of spectroscopy.

33. A method for diagnosis of cancer which comprises injecting a compound of claim 14 into an animal at a dosage of between 1 and 10 micromoles per kilogram of body weight of the animal and detecting locations of concentrated uptake of said compound by means of spectroscopy.

34. A method for diagnosis of cancer which comprises injecting a compound of claim 15 into an animal at a dosage of between 1 and 10 micromoles per kilogram of body weight of the animal and detecting locations of concentrated uptake of said compound by means of spectroscopy.

35. A method for diagnosis of cancer which comprises injecting a compound of claim 16 into an animal at a dosage of between 1 and 10 micromoles per kilogram of body weight of the animal and detecting locations of concentrated uptake of said compound by means of spectroscopy.

36. A method for diagnosis of cancer which comprises injecting a compound of claim 17 into an animal at a dosage of between 1 and 10 micromoles per kilogram of body weight of the animal and detecting locations of concentrated uptake of said compound by means of spectroscopy.

37. A method for diagnosis of cancer which comprises injecting a compound of claim 18 into an animal at a dosage of between 1 and 10 micromoles per kilogram of body weight of the animal and detecting locations of concentrated uptake of said compound by means of spectroscopy.

38. A method for diagnosis of cancer which comprises injecting a compound of claim 19 into an animal at a dosage of between 1 and 10 micromoles per kilogram of body weight of the animal and detecting locations of concentrated uptake of said compound by means of spectroscopy.

* * * * *

UNITED STATES PATENT AND TRADEMARK OFFICE
CERTIFICATE OF CORRECTION

PATENT NO. : 6,103,751
DATED : August 15, 2000
INVENTOR(S) : Ravindra K. Pandey, et al.

It is certified that error appears in the above-identified patent and that said Letters Patent is hereby corrected as shown below:

Column 20, claim 9,
Line 23, please insert a "C" between the - and the (O) so that the formula reads:
-- $C(O)N((CH_2)_5CH_3)C(O)$ --.

Column 20, claim 10,
Line 28, please insert a "C" between the - and the (O) so that the formula reads:
-- $C(O)N((CH_2)_2CH_3)C(O)$ --.

Signed and Sealed this

Sixth Day of November, 2001

Attest:

*Nicholas P. Godici*

NICHOLAS P. GODICI
*Attesting Officer*     *Acting Director of the United States Patent and Trademark Office*